United States Patent [19]

Nitzsche et al.

[11] Patent Number: 4,577,630

[45] Date of Patent: Mar. 25, 1986

[54] REUSABLE BREACH LOADING TARGET PRESSURE ACTIVATED LANCET FIRING DEVICE

[75] Inventors: Raymond P. Nitzsche, Edison; Kenneth E. Geiger, Hackensack, both of N.J.

[73] Assignee: Becton, Dickinson and Co., Paramus, N.J.

[21] Appl. No.: 580,056

[22] Filed: Feb. 14, 1984

[51] Int. Cl.$^4$ ............................................. A61B 17/34
[52] U.S. Cl. .................................. 128/314; 128/329 R
[58] Field of Search .................. 128/314, 315, 329 R, 128/330, 770; 604/136, 137, 157

[56] References Cited

U.S. PATENT DOCUMENTS

| | | | |
|---|---|---|---|
| 3,030,959 | 4/1962 | Grunert | 128/314 X |
| 3,046,987 | 7/1962 | Ehrlich | 128/314 |
| 3,358,689 | 12/1967 | Higgins | 128/329 R |
| 4,157,086 | 6/1979 | Maiorano et al. | 128/314 X |
| 4,230,118 | 10/1980 | Holman et al. | 128/314 |
| 4,416,279 | 11/1983 | Linder et al. | 128/314 |
| 4,449,529 | 5/1984 | Burns et al. | 128/314 |
| 4,503,856 | 3/1985 | Cornell et al. | 128/314 |

OTHER PUBLICATIONS

"Autoclix" Instruction Pamphlet.

Primary Examiner—Michael H. Thaler
Attorney, Agent, or Firm—John L. Voellmicke

[57] ABSTRACT

A reusable breach loading target pressure activated lancet firing device for use with a lancet includes a sled which releasably engages the lancet so that the lancet point may extend outwardly from a distal end of the sled. The sled is substantially contained and movably engaged within a housing having a distal aperture at its distal end and a side aperture defining a breach to allow access to the sled for engaging and disengaging the lancet. A spring is provided for biasing the distal end of the sled toward the distal end of the housing. A cocking mechanism positions and releasably holds the sled in a position in a direction toward the proximal end of the housing so that the spring means is partially deflected. A trigger mechanism for releasing the cocking mechanism and allowing the sled to move toward the distal aperture, also allows the lancet, when engaged in the sled, to project outwardly from the distal aperture. The trigger mechanism is activated by contact pressure between the patient's skin and the trigger mechanism.

22 Claims, 13 Drawing Figures

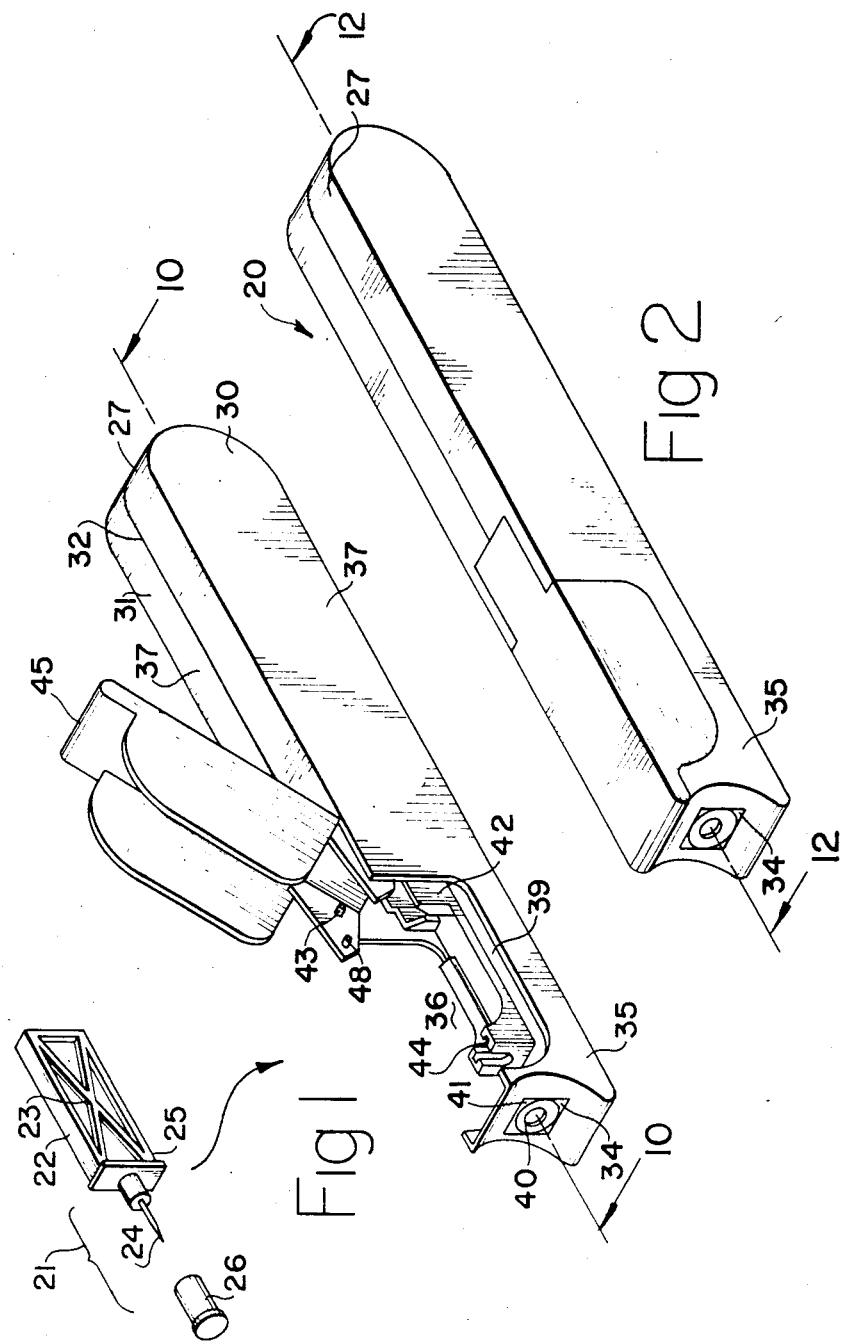

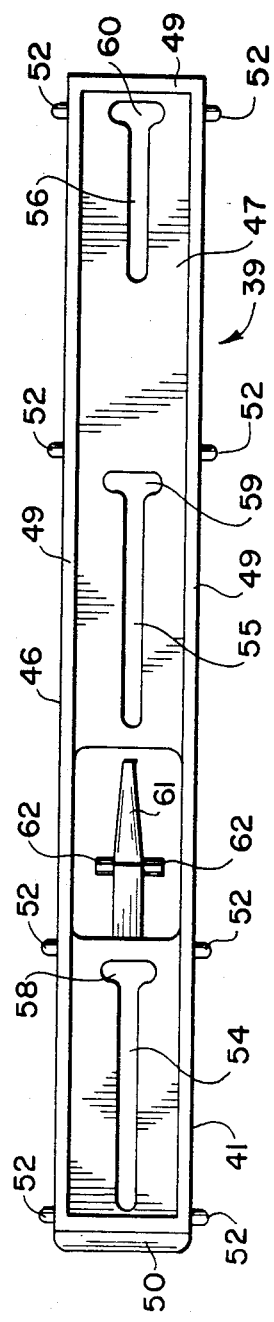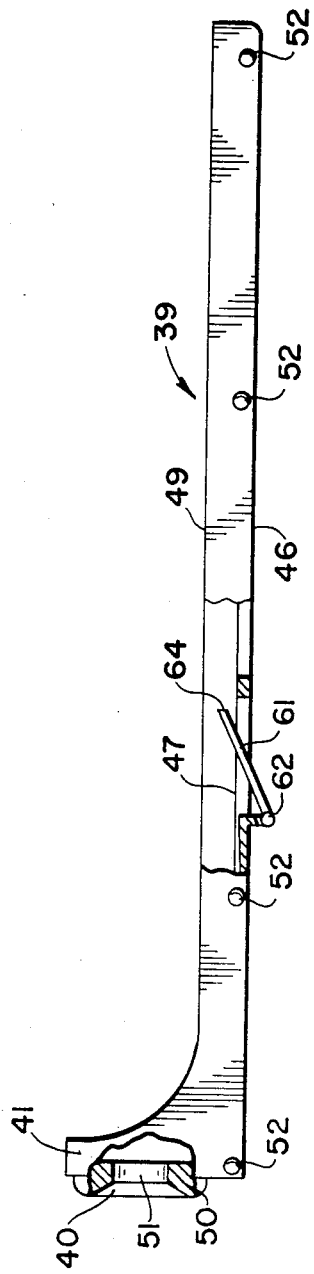
Fig 4
Fig 3

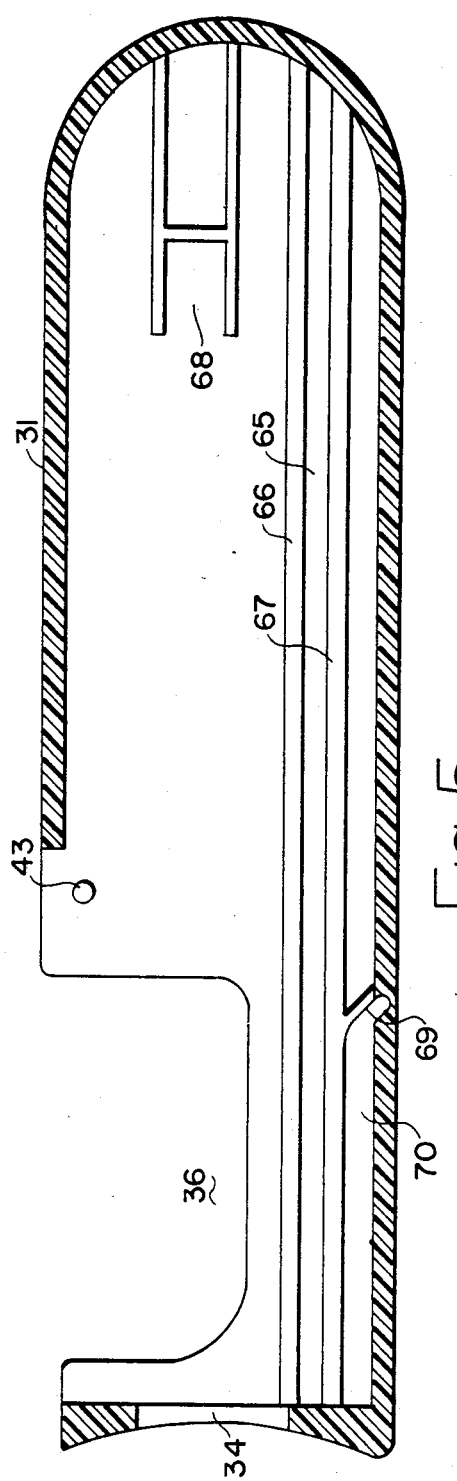

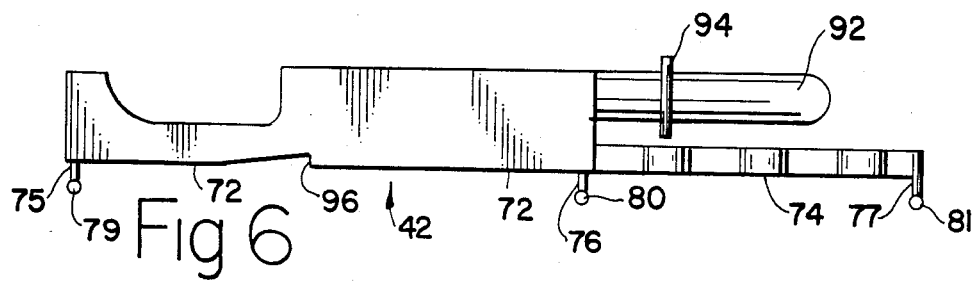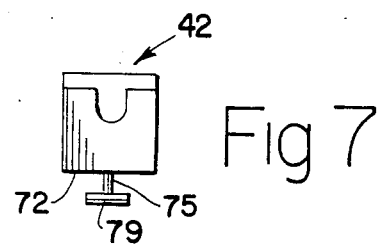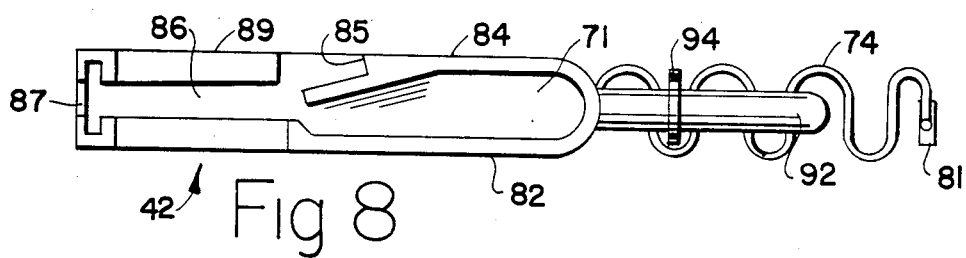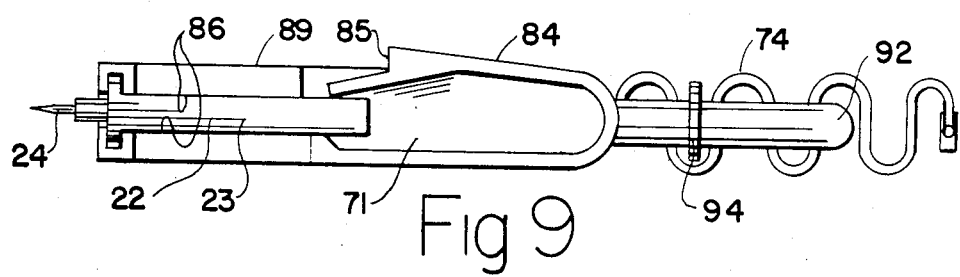

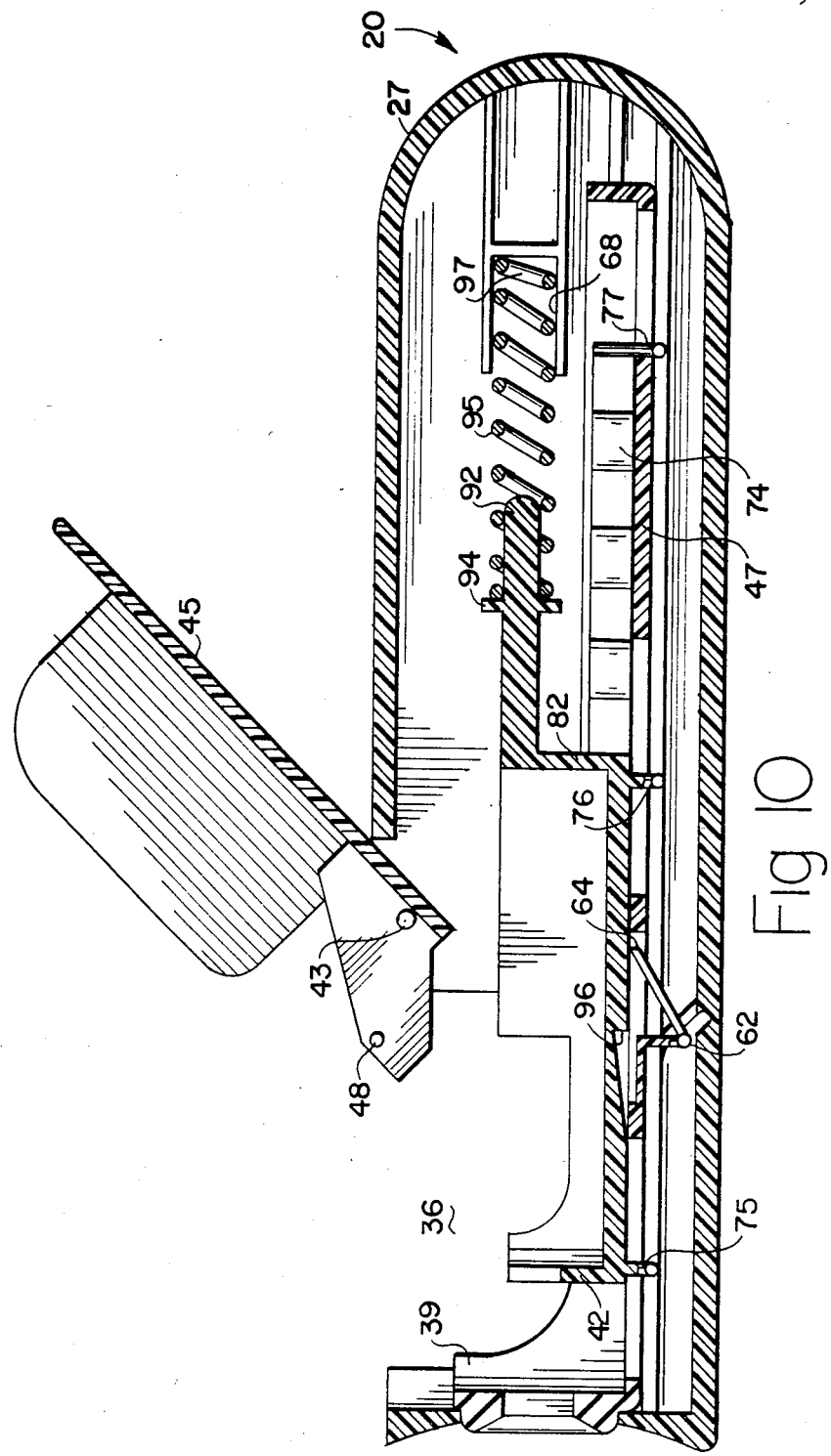

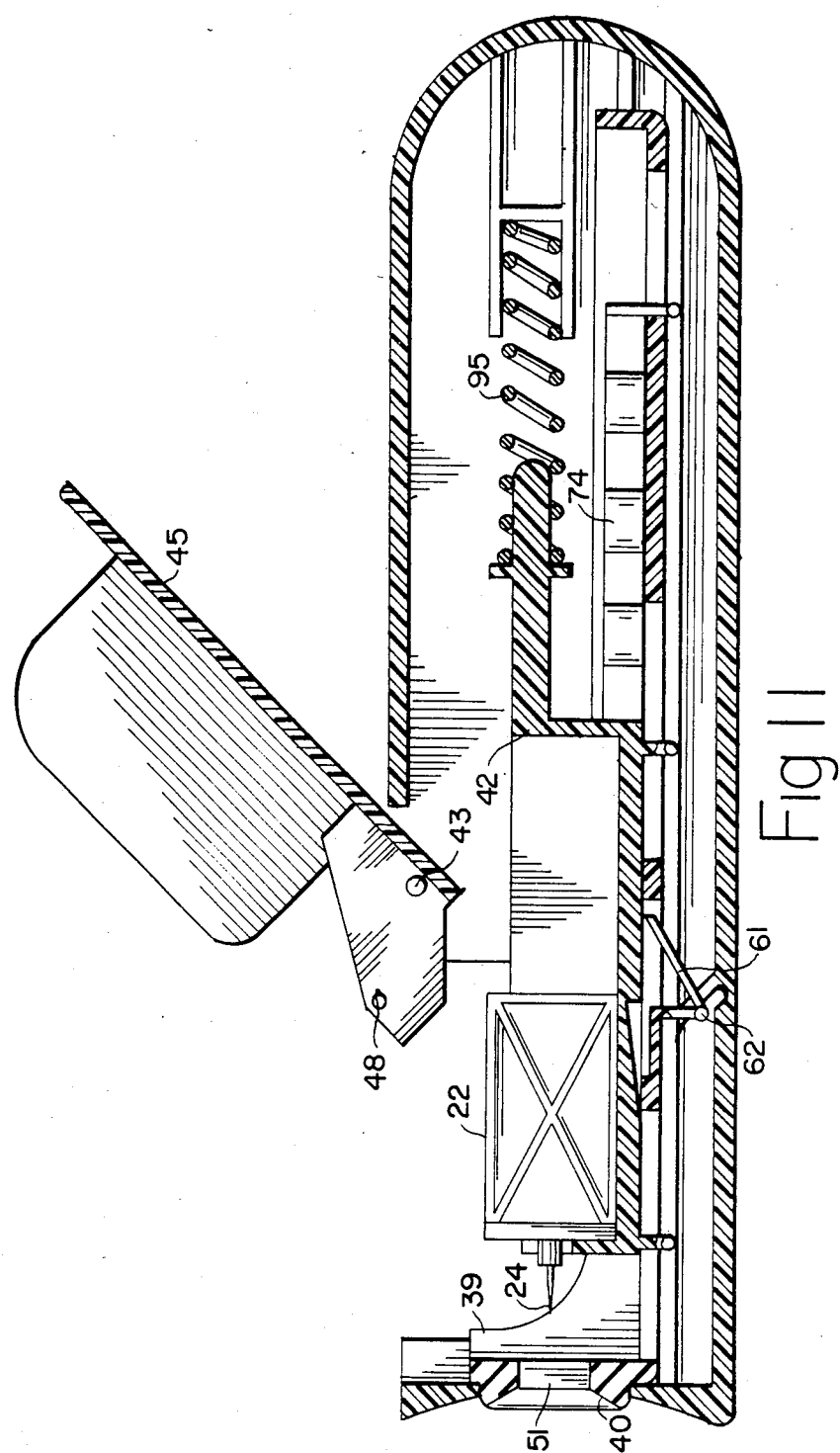

REUSABLE BREACH LOADING TARGET PRESSURE ACTIVATED LANCET FIRING DEVICE

BACKGROUND OF THE INVENTION

1. Field of the Invention

The present invention relates to a blood lancet firing device and more particularly relates to a reusable breach loading target pressure activated lancet firing device for penetrating living flesh to provide capillary blood for testing.

2. Description of the Prior Art

It is a common procedure in hospitals, clinics and doctor's offices to perform tests on blood provided by cutting or puncturing the skin and causing the capillaries of the patient to bleed. It is also common for persons afflicted with diabetes mellitus to frequently test their own capillary blood to determine blood glucose levels. The instrument used to cut the capillaries is called a lancet. The lancet typically includes a shank portion, which is formed to facilitate holding the lancet, and a sharp cutting portion. A lancet of this type, wherein the cutting portion is planar and V-shaped, is shown in U.S. Pat. No. 3,046,987 to Ehrlich. Another lancet design is shown in U.S. Pat. No. 3,358,689 to Higgins.

There is a certain amount of pain associated with producing capillary blood with a lancet since the skin at the patient's finger tips, which contains sensitive nerve endings, is severed to obtain the blood sample. Patient discomfort and apprehension are magnified by the sight of the lancet as it is thrust toward the skin by the doctor or nurse. These problems exist to a greater degree when the patient obtains his own blood sample since it is psychologically difficult to prick one's own finger tip with a lancet. Finger pricking with a hand held lancet can cause additional pain if the lancet is not thrust straight into and out of the patient. If the lancet cutting tip enters angularly or is moved while inside the patient, additional slicing and irritation of nerve endings will result. Also, pain from lancet finger pricks is reduced if the lancet is quickly removed from the patient's finger.

Automatic lancet devices offer improvements regarding some of the above mentioned physical and psychological problems in that they automatically propel the lancet tip into and out of the patient. U.S. Pat. No. 4,230,118 to Holman et al. teaches a reusable automatic lancet device which includes a disposable mounted needle to perform the lancet function. The Holman et al. device has a spring driven arm which is pivoted at one end in a housing while its other end protrudes through an arcuate slot in the housing. The mounted needle is placed in a holder portion at the end of the arm so that the needle is positioned tangentially to the arcuate slot. The arm may then be rotated clockwise to engage a latch. Approximately 90° in a counterclockwise direction from the latch is a finger rest with a hole therein. When the patient's finger is placed against the finger rest covering the hole and a trigger is deflected, the arm drives the needle through the arcuate path causing the needle to enter the hole in the finger rest, penetrate the finger and then become withdrawn.

The Holman et al. automatic lancet device has several deficiencies. Most noteworthy is that when the mounted needle is loaded into the arm, the needle is facing the user's hand. This front loading procedure offers the potential for contamination of the needle point and accidental skin puncture during loading and unloading of the lancet. Also, the needle in the Holman et al. device travels in an arcuate path and therefore enters the skin at an angle, slicing through the skin, rather than entering straight in along its longitudinal axis. Further, it is believed that the separate operation of pressing the trigger tends to set the lancet device in motion further adding to the potential for slicing motions while the needle is in the patient's skin. Finally, the lancet's motion toward the patients skin is still visible.

Another automatic lancet device is manufactured in West Germany and sold in the United States under the trade name AUTOCLIX, by BIO-DYNAMICS Company of Indianapolis, Ind. The AUTOCLIX device works with a disposable lancet similar to that described in the aforementioned patent to Higgins. The AUTOCLIX device is a relatively large rectangular structure with rounded corners which is held in the user's hand so that an external plunger is manipulable by the thumb while the end with a pressure platform projects outwardly from the other side of the user's hand. In use, the plunger is depressed to load the spring mechanism and to allow the front loading insertion of a lancet, with protective tip installed, through a hole in the pressure platform. The tip is then removed to expose the sharp lancet point and the plunger released to retract the lancet into the structure. Placing the patient's finger tip over the pressure platform hole and applying force on the pressure platform, with that finger, will activate the device causing the lancet point to momentarily protrude through a hole in the pressure platform penetrate the finger tip and to retract therefrom. After use, the plunger is again pressed causing the sharp lancet point to protrude from the pressure platform hole and to be ejected if the point is directed downwardly. The lancet tip should then be reinstalled over the lancet point.

Although complex in structure, the AUTOCLIX device offers the advantage of target pressure activation, i.e., the finger which will be pierced by the lancet point provides the force to activate the firing mechanism. Target pressure activation is desirable in a lancet device where the lancet point moves into and out of the user's flesh in a straight line, rather than in an arcuate path as provided by Holman et al., because the activation forces are in a direction which is approximately parallel to the motion of the lancet and these forces have less tendency to produce a tilting or twisting of the lancet device while the lancet is in motion and therefore reduces the potential for slicing action by the lancet point while it is in the user's finger. Also, the AUTOCLIX device shields the lancet motion from the patient's view. However, this lancet device still has deficiencies in that it must be front loaded thus exposing the lancet tip to accidental contamination and the user to accidental skin puncture. In addition, this device fires regardless if there is a lancet installed or not.

U.S. Pat. No. 4,416,279 to Lindner et al. teaches a lancet device which allows breach loading of the lancet into a lancet holding member. The Lindner et al. device is grasped by the user so that it is held between the thumb and the finger to be penetrated by the lancet. In use, the user, with his free hand, rotates an operating cylinder, which is concentric with the main body of the device, until the lancet holding member retracts to a low position where the lancet may be installed. Movement of the lancet holding member is caused by a guide pin or follower which is connected to the lancet holding member and rides on a cam path within the operating cylinder. Movement of the follower along the cam path also compresses a drive spring. After lancet installation, further rotation of this operating cylinder causes further compression of the drive spring. Compression of the drive spring continues until the cam path abruptly ends and the lancet holding member is propelled toward the user's finger. Although the Lindner et al. device offers the advantage of breach loading, it still is deficient in that motion of the lancet or structure associated with the lancet is visible to the user. Also, activation of the Lindner et al. device via twisting of the operating cylinder makes it difficult to maintain a constant positional relationship between the device and the user's finger. Accordingly, this twist activation is believed to add to the potential for slicing motions while the lancet point is in the patient's skin.

Although various forms of automatic lancet devices have been addressed by the prior art, there is still a need for a simple, straight-forward, easily fabricated reusable lancet firing device which is breach loading, target pressure activated and which propels the lancet point straight into and out of the patient's flesh. It is also desirable to provide a lancet firing device with structure to shield the motion of the lancet from the patient's view.

SUMMARY OF THE INVENTION

The reusable breach loading target pressure activated lancet firing device of the present invention, for use with a lancet having a handle portion and a point, comprises a sled including means for releasably engaging the lancet so that, upon loading, the lancet point extends outwardly from a distal end of the sled and a housing including an aperture through a distal end thereof. The sled is substantially contained within the housing and movably engaged therein. This housing further includes a side aperture to allow access to the sled for engaging and disengaging the lancet. Also provided is a means for biasing the distal end of the sled toward the distal end of the housing and a cocking means for positioning and releasably holding the sled in a position in a direction toward the proximal end of the housing so that the biasing means is energized. The cocking means includes a trigger means for releasing the cocking means and allowing the sled to move toward the distal aperture and allowing the lancet point, when the lancet is engaged in the sled, to project outwardly from the distal aperture. This trigger means is responsive to contact pressure between the patient's skin in an area adjacent to the site of the intended skin puncture and the trigger means.

In accordance with another embodiment of the present invention, a reusable breach loading target pressure activated lancet firing device for use with a lancet including a handle portion and a lancet point extending outwardly from a distal end of the handle comprises a hollow housing including a distal end, a proximal end and a side wall therebetween. This housing has an aperture in the distal end and a side aperture defining a breach in the sidewall. A trigger member is slidably engaged in the housing and has a distal end extending outwardly from the distal aperture. A sled slidably engaged within the housing, adjacent to the trigger member, includes a lancet engagement means for releasably engaging the lancet handle portion in order to permit the lancet point to extend outwardly from the distal end of the sled when the lancet is engaged thereon. This sled is capable of sliding to a first rest position with the lancet engaging means being accessible from the side aperture of the housing. The lancet point is maintained internally of the distal aperture when the lancet handle portion is engaged in the lancet engaging means and the sled is in the first position. Also included is a spring means positioned in the housing for biasing the distal end of the sled toward the distal end of the housing and sear means for holding the sled in a second position in a direction toward the proximal end of the housing so that the spring means is partially deflected. A side hood substantially covering the side aperture of the housing is movably engaged to the housing so that the hood may be opened to expose the lancet engagement means. A drive pin projects inwardly from the side hood and a means for accepting this drive pin is included on the sled so that closure of the side hood causes the drive pin to travel in a path to engage the drive pin accepting means and move the sled toward the proximal end of the housing, deflect the spring means and engage the sear means. A trigger means is provided for releasing the sear means and allowing the sled to slide toward the distal aperture to a third position. At this third position, the sled is closer to the distal end of the housing than in the first position. Also, the lancet point, when the lancet handle portion is engaged in the lancet engaging means is positioned outwardly from the distal aperture of the housing when the sled is in this third position. The activation of the trigger means is responsive to contact pressure between the patient's skin in an area adjacent to the site of the intended skin puncture and the trigger means. It is at the third position, as will be shown in more detail hereinafter, that the lancet point is positioned so that it can penetrate the patient's skin to sever capillaries and produce the desired blood sample for testing.

A number of advantages and objectives are attained consistent with the principles of the present inventions. Primarily, the present invention provides a simple, straight-forward, easily fabricated reusable lancet firing device which is breach loaded to minimize accidental contamination and skin puncture, and target pressure activated to minimize rocking or twisting motion of the lancet firing device while the lancet point is in the patient's flesh. Also, the present invention propels the lancet point straight into and out of the patient's flesh to avoid the slicing action of devices which propel the lancet in an arcuate path. Further, an embodiment of the present invention provides structure to shield the motion of the lancet from the patient's view.

BRIEF DESCRIPTION OF THE DRAWINGS

FIG. 1 is a perspective view of the preferred lancet firing device with side hood opened, also illustrating a disposable lancet assembly with shield removed from the handle portion;

FIG. 2 is a perspective view of the preferred lancet firing device with the side hood closed;

FIG. 3 is an enlarged side elevation view of the preferred trigger member of the present device partially cut away to show the cantilevered trigger sear member and the patient contact surface;

FIG. 4 is an enlarged top plan view of the preferred trigger member of FIG. 3;

FIG. 5 is an enlarged side elevation view of the right housing portion of the preferred lancet firing device;

FIG. 6 is an enlarged side elevation view of the sled of the preferred lancet firing device;

FIG. 7 is an enlarged front elevation view of the sled of FIG. 6;

FIG. 8 is an enlarged top plan view of the sled of FIG. 6;

FIG. 9 is an enlarged top plan view of the sled of FIG. 6 with a lancet installed;

FIG. 10 is an enlarged cross-sectional view of the preferred lancet firing device taken substantially along line 10—10 of FIG. 1;

FIG. 11 is an enlarged cross-sectional view of the lancet firing device of FIG. 10 further showing a lancet installed;

DETAILED DESCRIPTION

Figure 12:
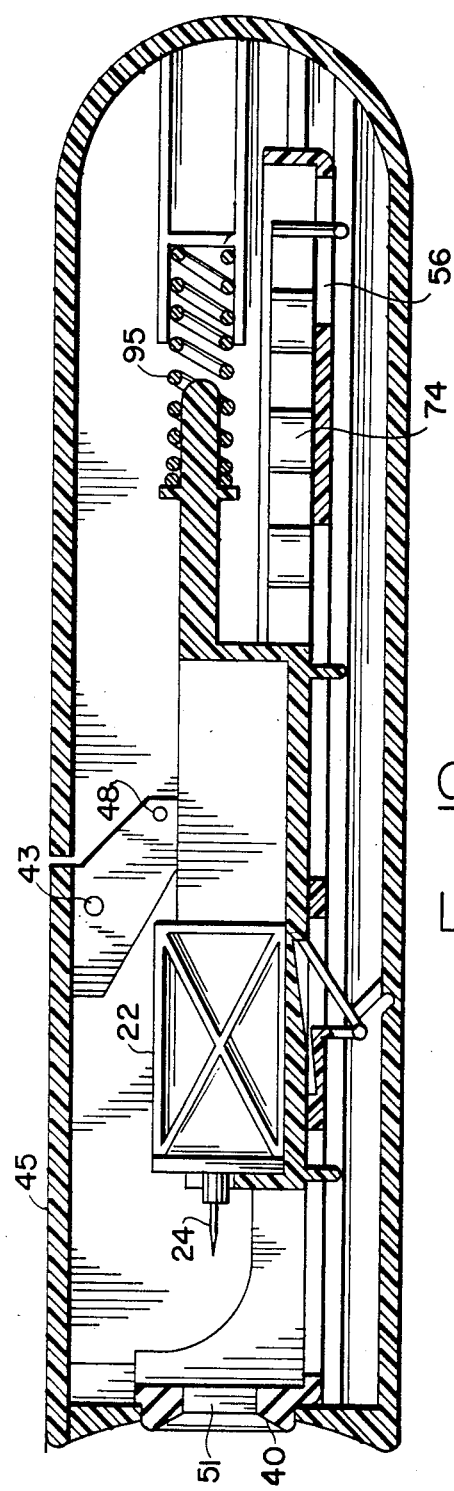
FIG. 12 is an enlarged cross-sectional view of the preferred lancet firing device taken substantially along line 12—12 of FIG. 2.

While this invention is satisfied by embodiments in many different forms, there is shown in the drawings and will herein be described in detail a preferred embodiment of the invention with the understanding that the present disclosure is to be considered as exemplary of the principles of the invention and is not intended to limit the invention to the embodiment illustrated. The scope of the invention will be measured by the appended claims and their equivalents.

Adverting to FIGS. 1 and 2, a reusable breach loading target pressure activated lancet firing device 20 is suitably used with a disposable lancet assembly 21. The disposable lancet assembly, in the embodiment being described, includes a lancet 22 having a handle portion 23, a lancet point 24 extending outwardly from a distal end 25 of the handle portion and a removable shield 26 for protectively covering lancet point. The sharp lancet point is adapted to pierce the patient's skin, severing capillaries, to provide blood for diagnostic testing. Shield 26 protects the cleanliness and sharp edges of the lancet before use. The shield may be reinstalled after use to protect the patient and subsequent handlers from inadvertent skin puncture.

Lancet firing device 20 preferably includes a hollow housing 27, including a left housing portion 30 and a right housing portion 31 joined along surface 32. These housing portions may be joined together via fasteners, adhesives, welding or other suitable means with sonic welding being preferred. Housing 27 also includes front aperture 34 at a distal end 35 of the housing and a side aperture 36 in a side wall 37 of the housing. It will be apparent to one skilled in the art that numerous constructions can be used to form a hollow housing and that the arrangement described is exemplary of the many possibilities. Housing 37 contains a trigger member 39 and a sled 42 both slidably engaged within the housing. Trigger member 39 includes a patient contact surface 40 at a distal end 41 thereof extending outwardly from the front aperture of the housing. Sled 42 includes a lancet engaging structure 44 for releasably engaging the lancet handle, which will be described in more detail hereinafter. Lancet engaging structure 44 is accessible from side aperture 36 which may be covered by a side hood 45 pivotally engaged to the housing through housing hinge pins 43 which project through corresponding apertures in the hood. Side hood 45 further includes a sled drive pin 48 projecting inwardly.

Turning now to FIGS. 3 and 4, trigger member 39, in this preferred embodiment, includes an elongate body portion 46 having a substantially planar bottom wall 47, a raised peripheral side wall 49 and a face plate 50 on distal end 41. This face plate includes smooth concave patient contact surface 40 and an aperture 51 extending therethrough. Outwardly projecting side pins 52 are provided on two sides of the trigger member to slidably engage the housing portions as will be explained in detail hereinafter. Sled engaging slots 54, 55 and 56 having enlarged proximal end portions 58, 59 and 60, respectively, are provided in bottom wall 47. A cantilevered trigger sear member 61 is preferably integrally formed with the bottom wall and includes cam follower pins 62 and flat sear surface 64.

Referring now to FIG. 5, the interior of the preferred right housing portion 31 includes a channel 65 for accepting trigger member side pins 52 to allow the trigger member to slide longitudinally within the housing along pathway 65. Channel 65 is defined by channel ribs 66 and 67 which are substantially parallel to each other and spaced apart a distance greater than the diameter of trigger member side pins 52. A cam path clearance groove 70 is provided for containing cam follower pin 62 of trigger sear member 61. A cam path 69, at the proximal end of groove 70, is provided for engaging cam follower pin 62 when the trigger member is moved toward the proximal end of the housing. Housing hinge pin 43, located adjacent to side aperture 36, projects inwardly and is provided to engage a corresponding hinge hole in side hood 45 allowing the side hood to be swung from an open to a shut position and back again. A flat bottomed spring receptacle 68 is also provided in the right housing portion. Left housing portion 30, although not illustrated in detail herein, contains similar pins, channels, ribs and grooves as described above so that when the housing halves are joined, the trigger member 39 is slidable within the housing and side hood 45 is rotatably connected therewith.

Turning now to FIGS. 6 through 10, the preferred sled 42 includes an oblong bottom wall 71 having a substantially flat bottom surface 72, a recoil tension spring 74 extending from the proximal end of the bottom wall in a direction substantially parallel to the longitudinal axis of bottom wall 71. Downwardly projecting posts 75, 76 and 77, with preferably integral perpendicular crossbars 79, 80 and 81, respectively, extend from bottom surface 72 and recoil spring 74. The length of posts 75, 76 and 77 should be greater than the thickness of bottom wall 47 of trigger member 39. The crossbars 79, 80 and 81 are small enough to fit through enlarged end portions 58, 59 and 60 of the trigger member but longer than the width of slots 54, 55 and 56 in the trigger member when the sled and trigger member are assembled. Sled 42 is narrow enough to fit within raised peripheral side wall 49 of the trigger member and may be slidably engaged in the trigger member by passing crossbars 79, 80 and 81 through enlarged portions 58, 59 and 60 and then sliding the sled toward the distal end of the trigger member. At this position, bottom surface 72 of the sled contacts the top surface of bottom wall 47 of the trigger member so that the sled is free to slide longitudinally along the trigger member but is retained on the trigger member by the crossbars.

In order to receive and releasably hold disposable lancet 22, sled 42 is preferably provided with rigid wall 82, flexible cantilevered side wall 84 with external sled follower ledge 85, lancet engaging slot 86 and lancet aperture 87. As best seen in FIG. 9, the lancet is inserted into the sled so that lancet point 24 extends outwardly past the distal end of the sled. Handle portion 23 of the lancet is releasably held in position by a frictional interference fit betwen the handle portion and engaging slot 86. Also, insertion of the lancet handle into the engaging slot deflects side wall 84 and causes ledge 85 to be positioned outwardly from the right side 89 of the sled. A spring positioning stud 92, as seen in FIGS. 6, 8 and 9, with a flange 94 projects from the proximal end of rigid wall 82 in a direction substantially parallel to the longitudinal axis of bottom wall 71. As best seen in FIG. 10, a compression spring 95 is contained at its proximal end 97 by housing spring receptacle 68 and at its distal end by stud 92 and flange 94 of the sled. A flat sear surface 96 is positioned substantially perpendicularly to flat bottom surface 72 of the sled. Sear surface 96 is adapted to engage sear surface 64 of the trigger sear member as will be hereinafter explained.

The preferred embodiment of the present invention as described above is assembled by: engaging the sled onto the trigger, as previously described; placing the compression spring on the compression spring stud; placing the subassembly of the trigger, sled and spring into one of the housing portions so that trigger side pins 52 are in the housing pathway 65 and cam follower pin 62 is in clearance groove 70; engaging the side hood with housing hingepin 43; and fixedly securing the remaining housing portion to the first housing portion. The relationship of the assembled components of the preferred breach loading target pressure activated lancet firing device is best seen in FIG. 10.

Referring to FIGS. 10 and 11 it should be noted that sled 42 is at its intermediate rest position and the lancet engaging structure is readily accessible through side aperture 36 so that a lancet may be installed or removed from the sled structure. The capacity of the instant lancet firing device to allow installation and removal of the lancet through the side aperture is referred to as breach loading. This is an important feature of the instant invention because it allows the lancet to be held by its handle while it is being installed or removed from the lancet firing device, thereby substantially reducing the possibility of contamination and infection due to accidental skin puncture. Also, it should be noted that at the rest position neither compression spring 95 nor recoil spring 74 is in a stressed state.

Adverting to FIGS. 1 and 9 through 13, in use, the patient, doctor, nurse, technician or other qualified person, hereinafter referred to as the user, opens side hood 45 to expose sled 42. Then shield 26 is removed from the lancet assembly 21 and the lancet is inserted into the lancet engaging slot of sled 42 so that cantilever side wall 84 of the sled is deflected outwardly as best seen in FIG. 9. The user may now close the side hood. The initial closing action of the side hood causes sled drive pin 48 on the hood to travel in an arcuate path engaging sled follower ledge 85 and forcing the sled toward the proximal end of the housing compressing compression spring 95 and allowing flat sear surface 64 of cantilever trigger member 61 to engage sear surface 96 of the sled thus holding the compression spring in a compressed position and preventing motion of the sled toward the distal end of the housing. Further closing motion of the side hood causes the drive pin to continue on its arcuate path disengaging ledge 85 when the drive pin moves upwardly above the sled as best shown in FIG. 12. FIG. 12 also shows the sled in its second, or loaded, position with compression spring 95 compressed and recoil spring 74 still in an unstressed or relaxed state. At this point, the present lancet firing device is ready for use to produce a blood sample.

Figure 13:
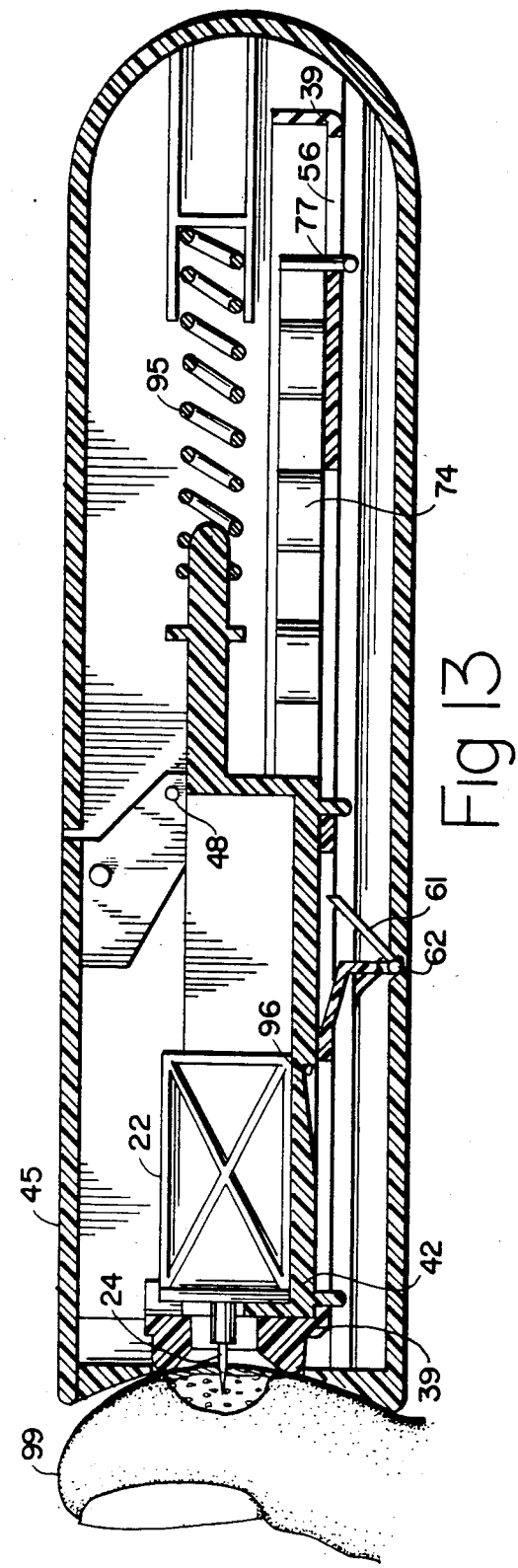
FIG. 13 is an enlarged cross-sectional view of the lancet firing device of FIG. 12 with the trigger member and sled shown in the position with the lancet tip projecting outwardly through the face plate aperture penetrating the patient's skin.

To activate the lancet firing device, the user places a finger on patient contact surface 40 and presses the finger against the trigger member moving it toward the proximal end of the housing. The motion of the trigger member also moves cam follower pin 62 along clearance groove 70 into contact with housing cam path 69. The cam path is directed downwardly away from the longitudinal axis of the trigger member thus pulling cantilevered trigger sear member 61 downwardly and causing sear surface 64 to disengage sear surface 96 in the sled. With the sear surfaces disengaged, the sled, with lancet engaged, is propelled by compression spring 95 straight toward the distal end of the housing. The momentum of the sled causes it to contact face plate 50 of the trigger member at which position lancet point 24 projects outwardly through aperture 51 in face plate 50 as best seen in FIG. 13. At this position, the lancet point has entered the flesh of finger 99 severing capillaries to produce the blood sample. Also, at this position recoil spring 74 is stressed in tension, possessing enough recoil energy to thereafter, in quick fashion, pull the sled and lancet toward the proximal end of the housing to the neutral position. The tension forces in spring 74 are caused by downwardly projecting post 77 engaging the distal end of slot 56 in the trigger member so that the end of tension spring 74 containing post 77 cannot move toward the distal end of the housing while the rigid portion of the sled is propelled in that direction by spring 95.

It should be noted that the lancet is carried to and from the skin puncture site along a straight line so that the lancet point pierces the skin but does not slice through it like prior art devices which require the lancet to travel through a traumatizing arcuate path. After retraction of the lancet point, the side hood may be opened and the lancet removed, and then reshielded to protect the user from accidental cutting, and then properly discarded. The lancet firing device may now be used again for producing blood samples by repeating the above described steps. It should be noted that it is a feature of the preferred embodiment that if a lancet is not placed in the sled, follower ledge 85 will not be deflected outwardly into the path of sled drive pin 48 and the sled will not be driven toward the distal end of the housing to the loaded position. Accordingly, the preferred lancet firing device will not perform in a Russian roulette fashion because it will not function without a lancet installed. If necessary, the user may load, use and unload the preferred lancet firing device using one hand only. This is a beneficial feature since many diabetics suffer from neuropathy, a degeneration of nerve and motor functions of the extremities.

A wide variety of rigid materials are suitable for fabricating housing portions 30 and 31, however, thermoplastic materials such as ABS, polycarbonate and polystyrene are preferred. It is preferred that side hood 25, sled 42 and trigger member 39 be made of a plastic material with acetal resin being preferred. It is also preferred that recoil spring 74 be integrally formed with sled 42 and that cantilever trigger sear member 61 be integrally formed with trigger member 39. It is preferred that compression spring 95 be made of stainless steel wire.

Thus, it can be seen that the present invention provides a simple, straight-forward, easily fabricated reusable lancet firing device. Most importantly, the present invention provides a lancet firing device which can be breach loaded through a side aperture to reduce the possibility of contamination and accidental cutting associated with front loading devices while being target pressure activated to minimize the rocking or twisting motion of the lancet firing device while the lancet point is in the patient's flesh. The present invention propels the lancet straight into and out of the patient's flesh to avoid the slicing action of devices which propel the lancet in an arcuate path. Further, the preferred embodiment of the present invention provides structure to shield the motion of the lancet from the patient's view and can be operated with one hand, if necessary. Also, the preferred embodiment of the present invention will not function without a lancet installed.

What is claimed is:

1. A reusable breach loading target pressure activated lancet firing device for use with a lancet including a handle portion and a lancet point extending outwardly from a distal end of the handle portion comprising:
   a hollow housing including a distal end, a proximal end and a side wall therebetween, said housing having an aperture in said distal end and a side aperture defining a breach in said side wall;
   a trigger member movably engaged in said housing having a distal end extending outwardly from said distal aperture;
   a sled slidably engaged within said housing adjacent to said trigger member including lancet engagement means for releasably engaging the lancet handle portion in order to permit the lancet point to extend outwardly from a distal end of said sled when the lancet is engaged therein, said sled capable of sliding to a first rest position with said lancet engagement means being accessible from said side aperture, the lancet point being maintained internally of said distal aperture when the lancet handle portion is engaged in said lancet engagement means and said sled is in said first position;
   a side hood substantially covering said side aperture, said hood being movably engaged to said housing so that said hood may be opened to expose said lancet engagement means;
   spring means positioned in said housing for biasing the distal end of said sled toward the distal end of said housing;
   sear means for holding said sled in a second position in a direction toward said proximal end of said housing so that said spring means is partially deflected and cooperating means on said side hood and said sled for facilitating the movement of said sled toward said proximal end of said housing, deflecting said spring means and engaging said sear means; and
   trigger means for releasing said sear means and allowing said sled to slide toward said distal aperture to a third position, said sled being closer to said distal end of said housing in said third position than in said first position, the lancet point, when the lancet handle portion is engaged in said lancet engagement means, being positioned outwardly from said distal aperture when said sled is in said third position, the activation of said trigger means being responsive to contact pressure between the patient's skin in an area adjacent to the site of the intended skin puncture and said trigger member.

2. The lancet firing device of claim 1 wherein said sear means includes a drive pin projecting inwardly from said side hood and drive pin accepting means on said sled, wherein closure of said side hood causes said drive pin to travel in a path to engage said drive pin accepting means and move said sled toward said proximal end of said housing, deflecting said spring means and engaging said sear means.

3. The lancet firing device of claim 2 wherein said sear means includes a cantilever member projecting outwardly from said trigger member toward said proximal end of said housing pressing against said sled and an engaging recess in said sled positioned so that when said sled is in said second position said cantilever member engages said engaging recess preventing said sled from moving toward said distal end of said housing.

4. The lancet firing device of claim 3 wherein said cantilever member is an integral part of said trigger member.

5. The lancet firing device of claim 3 wherein said trigger means includes a cam surface projecting inwardly from said side wall of said housing, a cam surface follower projecting outwardly from said cantilever member and engaging said cam surface, said cam surface being shaped so that movement of said trigger member toward said proximal end of said housing forces said follower and said cantilever in a direction away from said engaging recess thus disengaging said cantilever from said recess and allowing said spring means to move said sled to said third position.

6. The lancet firing device of claim 2 wherein said drive pin accepting means includes a flexible drive pin accepting member projecting outwardly from said sled and being positioned outside of said path of said drive pin, whereby engagement of the lancet handle portion into said lancet engagement means deflects said drive pin accepting member into said path of said drive pin, said cocking means being operative only where said lancet is engaged in said lancet engagement means.

7. The lancet firing device of claim 1 wherein said spring means includes a compression spring in an uncompressed condition when said sled is in said first position.

8. The lancet firing device of claim 1 further including a recoil means for returning said sled from said third position to said first position.

9. The lancet firing device of claim 8 wherein said recoil means includes a recoil tension spring positioned between said sled and said trigger member and being unstressed when said sled is in said first position, said recoil spring being stressed when said sled is in said third position and possessing enough energy to return said sled to said first position.

10. The lancet firing device of claim 9 wherein said recoil tension spring is an integral part of said sled.

11. The lancet firing device of claim 1 wherein said trigger member, said sled and said hood are made of thermoplastic material.

12. The lancet firing device of claim 11 wherein said thermoplastic material is acetal.

13. The lancet firing device of claim 1 wherein said housing is made of thermoplastic material.

14. A reusable breach loading target pressure activated lancet firing device for use with a lancet including a handle portion and a point comprising:

a sled including means for releasably engaging the lancet so that, upon loading, the lancet point extends outwardly from a distal end of said sled;

a housing including an aperture through a distal end of said housing, said sled being substantially contained within said housing and movably engaged therein, said housing further including a side aperture to allow access to said sled for engaging and disengaging the lancet;

means for biasing the distal end of said sled toward the distal end of said housing;

a side hood substantially covering said side aperture, said hood being movably engaged to said housing so that said hood may be opened to expose said lancet engagement means; and cocking means for positioning and releasably holding said sled in a position in a direction toward said proximal end of said housing so that said biasing means is energized, said cocking means including cooperating means on said sled and said side hood for facilitating the movement of said sled toward said proximal end of said housing, said cocking means including trigger means for releasing said cocking means and allowing said sled to move toward said distal aperture and allowing the lancet point, when the lancet is engaged in said sled, to project outwardly from said distal aperture, the activation of said trigger means being responsive to contact pressure between the patient's skin in an area adjacent to the site of the intended skin puncture and said trigger means.

15. A reusable breach loading target pressure activated lancet firing device for use with a lancet including a handle portion and a lancet point extending outwardly from a distal end of the handle portion comprising:

a hollow housing including a distal end, a proximal end and a side wall therebetween, said housing having an aperture in said distal end and a side aperture defining a breach in said side wall;

a trigger member movably engaged in said housing having a distal end extending outwardly from said distal aperture;

a sled slidably engaged within said housing adjacent to said trigger member including lancet engagement means for releasably engaging the lancet handle portion in order to permit the lancet point to extend outwardly from a distal end of said sled when the lancet is engaged therein, said sled capable of sliding to a first rest position with said lancet engagement means being accessible from said side aperture, the lancet point being maintained internally of said distal aperture when the lancet handle portion is engaged in said lancet engagement means and said sled is in said first position;

spring means positioned in said housing for biasing the distal end of said sled toward the distal end of said housing;

sear means for holding said sled in a second position in a direction toward said proximal end of said housing so that said spring means is partially deflected;

a side hood substantially covering said side aperture, said hood being movably engaged to said housing so that said hood may be opened to expose said lancet engagement means;

a drive pin projecting inwardly from said side hood;

means on said sled for accepting said drive pin so that closure of said side hood causes said drive pin to travel in a path to engage said drive pin accepting means and move said sled toward said proximal end of said housing, deflecting said spring means and engaging said sear means; and trigger means for releasing said sear means and allowing said sled to slide toward said distal aperture to a third position, said sled being closer to said distal end of said housing in said third position than in said first position, the lancet point, when the lancet handle portion is engaged in said lancet engagement means, being positioned outwardly from said distal aperture when said sled is in said third position, the activation of said trigger means being responsive to contact pressure between the patient's skin in an area adjacent to the site of the intended skin puncture and said trigger member.

16. The lancet firing device of claim 15 wherein said sear means includes a cantilever member projecting outwardly from said trigger member toward said proximal end of said housing pressing against said sled and an engaging recess in said sled positioned so that when said sled is in said second position said cantilever member engages said recess preventing said sled from moving toward said distal end of said housing.

17. The lancet firing device of claim 16 wherein said trigger means includes a cam surface projecting inwardly from said side wall of said housing, a cam surface follower projecting outwardly from said cantilever member and engaging said cam surface, said cam surface being shaped so that movement of said trigger member toward said proximal end of said housing forces said follower and said cantilever in a direction away from said engaging recess thus disengaging said cantilever from said recess and allowing said spring means to move said sled to said third position.

18. The lancet firing device of claim 15 wherein said spring means includes a compression spring in an uncompressed condition when said sled is in said first position.

19. The lancet firing device of claim 15 further including a recoil means for returning said sled from said third position to said first position.

20. The lancet firing device of claim 19 wherein said recoil means includes a recoil tension spring positioned between said sled and said trigger member and being unstressed when said sled is in said first position.

21. The lancet firing device of claim 15 wherein said drive pin accepting means includes a flexible drive pin accepting member projecting outwardly from said sled being positioned outside of said path of said drive pin, whereby engagement of the lancet into said lancet engagement means deflects said drive pin accepting member into said path of said drive pin, said sear means being engageable only when said lancet is engaged in said lancet engagement means.

22. A reusable lancet firing device comprising:
a lancet including a handle portion and a point;
a sled including means for releasably engaging the lancet so that the lancet point extends outwardly from the distal end of the sled;
a housing including an aperture through a distal end of said housing, said sled being substantially contained within said housing and movably engaged therein, said housing further including a side aperture to allow access to said sled for engaging and disengaging the lancet;
spring means for biasing the distal end of said sled toward the distal end of said housing;

a side hood substantially covering said side aperture, said hood being movably engaged to said housing so that said hood may be opened to expose said lancet engagement means; and cocking means for positioning and releasably holding said sled in a position in a direction toward said proximal end of said housing so that said spring means is energized, said cocking means including cooperating means on said sled and said side hood for facilitating the movement of said sled toward said proximal end of said housing, said cocking means including trigger means for releasing said cocking means and allowing said sled to move toward said distal aperture and allowing the lancet point to project outwardly from said distal aperture, the activation of said trigger means being responsive to contact pressure between the patient's skin in an area adjacent to the site of the intended skin puncture and said trigger means.

* * * * *